United States Patent
Weisse et al.

(10) Patent No.: US 12,070,030 B2
(45) Date of Patent: Aug. 27, 2024

(54) METHOD FOR CLEANING MEDICAL EQUIPMENT

(71) Applicant: BASF SE, Ludwigshafen am Rhein (DE)

(72) Inventors: Sebastian Alexander Weisse, Ludwigshafen am Rhein (DE); Bernhard Vath, Ludwigshafen am Rhein (DE); Tobias Heinz Steinke, Ludwigshafen am Rhein (DE); Robert D. Ober, Wyandotte, MI (US)

(73) Assignee: BASF SE, Ludwigshafen am Rhein (DE)

( * ) Notice: Subject to any disclaimer, the term of this patent is extended or adjusted under 35 U.S.C. 154(b) by 2 days.

(21) Appl. No.: 17/923,242

(22) PCT Filed: May 10, 2021

(86) PCT No.: PCT/EP2021/062271
§ 371 (c)(1),
(2) Date: Nov. 4, 2022

(87) PCT Pub. No.: WO2021/228739
PCT Pub. Date: Nov. 18, 2021

(65) Prior Publication Data
US 2023/0225312 A1 Jul. 20, 2023

(30) Foreign Application Priority Data
May 14, 2020 (EP) ..................... 20174553

(51) Int. Cl.
| | | |
|---|---|---|
| *A61L 2/235* | (2006.01) | |
| *A01N 25/10* | (2006.01) | |
| *A01N 25/16* | (2006.01) | |
| *A01N 31/02* | (2006.01) | |
| *A01N 59/16* | (2006.01) | |
| *B08B 1/10* | (2024.01) | |
| *C08J 9/00* | (2006.01) | |
| *C08J 9/14* | (2006.01) | |
| *A61L 101/02* | (2006.01) | |

(52) U.S. Cl.
CPC ............ *A01N 25/10* (2013.01); *A01N 25/16* (2013.01); *A01N 31/02* (2013.01); *A01N 59/16* (2013.01); *A61L 2/235* (2013.01); *B08B 1/10* (2024.01); *C08J 9/0066* (2013.01); *C08J 9/141* (2013.01); *A61L 2101/02* (2020.08); *A61L 2202/17* (2013.01); *A61L 2202/24* (2013.01); *C08J 2203/14* (2013.01); *C08J 2203/182* (2013.01); *C08J 2205/05* (2013.01); *C08J 2207/12* (2013.01); *C08J 2361/28* (2013.01)

(58) Field of Classification Search
CPC ........ A01N 25/10; A01N 25/16; A01N 31/02; A01N 59/16; A61L 2/235; A61L 2101/02; A61L 2202/17; A61L 2202/24; A61L 2/18; A61L 2101/34; A61L 2101/44; A61L 2101/48; B08B 1/10; C08J 9/0066; C08J 9/141; C08J 2203/14; C08J 2203/182; C08J 2205/05; C08J 2207/12; C08J 2361/28; C08J 9/40; C08L 61/28
See application file for complete search history.

(56) References Cited

U.S. PATENT DOCUMENTS

| | | | |
|---|---|---|---|
| 4,334,971 A | 6/1982 | Mahnke et al. | |
| 2006/0258763 A1 | 11/2006 | Baumgartl et al. | |
| 2010/0200017 A1 | 8/2010 | Kerr et al. | |
| 2011/0232680 A1* | 9/2011 | Gonzales | A47L 13/17 15/244.4 |
| 2012/0071578 A1 | 3/2012 | Baumgartl et al. | |
| 2015/0210814 A1* | 7/2015 | Gross | C08J 9/14 264/420 |
| 2017/0333156 A1 | 11/2017 | Ready et al. | |
| 2018/0140157 A1 | 5/2018 | Pung et al. | |

FOREIGN PATENT DOCUMENTS

| | | |
|---|---|---|
| EP | 0037470 B1 | 6/1985 |
| EP | 1505105 A1 | 2/2005 |
| WO | 01/94436 A2 | 12/2001 |
| WO | 2008/110475 A1 | 9/2008 |
| WO | 2009/136957 A1 | 11/2009 |
| WO | 2012/035457 A1 | 3/2012 |
| WO | 2014/037233 A1 | 3/2014 |
| WO | 2016/044821 A1 | 3/2016 |

OTHER PUBLICATIONS

International Search Report and Written Opinion received for PCT Patent Application No. PCT/EP2021/062271, mailed on Aug. 6, 2021, 13 pages.

* cited by examiner

*Primary Examiner* — Erin F Bergner
(74) *Attorney, Agent, or Firm* — Faegre Drinker Biddle & Reath LLP

(57) ABSTRACT

A method for cleaning medical equipment by scrubbing the equipment with an open-cell melamine-formaldehyde foam comprising an antibacterial active composition, and wherein the open-cell melamine-formaldehyde foam is prepared from a melamine-formaldehyde precondensate, wherein the molar ratio melamine to formaldehyde of the melamine-formaldehyde precondensate is smaller than 0.5.

8 Claims, No Drawings

METHOD FOR CLEANING MEDICAL EQUIPMENT

CROSS-REFERENCE TO RELATED APPLICATIONS

This application is a national stage application (under 35 U.S.C. § 371) of PCT/EP2021/062271, filed May 10, 2021, which claims benefit of European Application No. 20174553.6, filed May 14, 2020, both of which are incorporated herein by reference in their entirety.

The present invention relates to a method for cleaning medical equipment by scrubbing the equipment with a melamine-formaldehyde foam comprising an antibacterial active composition.

EP 1 505 105 A1 discloses shaped articles of melamine/formaldehyde foam having a formaldehyde emission of less than 0.1 ppm, determined according to DIN 55666, and are obtainable by the following process: a) a foam is prepared from a melamine/formaldehyde precondensate having a molar melamine: formaldehyde ratio greater than 0.5, b) the foam obtained is annealed at below 200° C., and c) the annealed foam is molded in a press at from 160 to 240° C. and an absolute pressure from 5 to 100 bar in the course of from 15 to 120 seconds to give the shaped article.

WO 01/94436 relates to a method for producing elastic foamed materials which are based on a melamine/formaldehyde condensation product. According to the inventive method, a pre-condensate, having a molar ratio of melamine to formaldehyde which is greater than 1:2, is foamed. Practically no emission of formaldehyde emanates from the foamed materials.

WO 2012/035457 and US 2012/071578 relate to processes for producing melamine-formaldehyde foams comprising the consecutive steps a) and b): a) heating a mixture comprising a melamine-formaldehyde precondensate, a curative and a blowing agent to foam up and crosslink said mixture, and b) tempering the foam obtained in step a), wherein it is essential to the present invention that—step a) utilizes a precondensate which has a melamine:formaldehyde molar ratio in the range from 1:2.1 to 1:3.9, and—which has a sulfite group content, based on the total weight of the melamine-formaldehyde precondensate, in the range from 0% to 1% by weight, and—said tempering in step b) is effected at a temperature in the range from 230 to 290° C., and also to melamine-formaldehyde foams obtainable according to the processes of the invention, and to uses thereof.

US 2018/140157 A1 discloses a cleaning implement made from a melamine-formaldehyde foam comprising from 0.1 to 5 wt.-% of at least on linear polymer with a number average molecular weight Mn in the range from 500 to 10,000 g/mol, preferably polyethylene glycol.

WO 2008/110475 relates to a method for the production of a foam comprising at least one antimicrobial active agent, comprising the following steps: (1) producing a solution or dispersion comprising at least one pre-condensate of the foam to be produced, and at least one antimicrobial active agent, (2) foaming the pre-condensate by heating the solution or dispersion from step (1) in order to obtain a foam having at least one antimicrobial active agent, and (3) tempering the foam obtained in step (2) at a temperature of 120 to 300° C. The foam produced in this manner can be used for the heat and sound insulation of buildings and building parts, for the heat and sound insulation of the interior spaces of vehicles and aircraft, for low temperature insulation, as an insulating wall covering, as an insulating and impact damping packaging material, as abrasively acting cleaning, grinding, and polishing sponges, in the hygiene sector, and as filter material.

WO 2014/037233 discloses a process for producing melamine-formaldehyde foams, said process comprising heating and foaming a mixture, comprising at least one melamine-formaldehyde precondensate, at least one curative, a surfactant mixture, at least one salt of an inorganic acid and/or of an organic carboxylic acid, at least one blowing agent using microwave radiation.

WO 2009/136957 discloses a contoured sterilizing element for wiping and sterilizing surfaces of a medical device including an anti-pathogenic agent and an absorbent, resilient article, such as a viscoelastic polyurethane foam.

US 2010/200017 discloses a microbial scrub brush with a semi-closed hydrophilic polyurethane medical grade foam insert that is impregnated with an antibacterial disinfectant.

WO 2016/044821 discloses methods and apparatus for cleaning a central venous catheter port. An apparatus includes a body, a coupling configured to connect the body to the hub, a cleaning cap coupled to the body, and an actuator disposed within the body for rotating and translating the cap relative to the hub. The cleaning cap includes a cap body defining a cavity and a cleaning member disposed within the cavity, the cleaning member having threads that engage with the threads on the hub.

US 2017/0333156 discloses systems for disinfecting Central Venous Catheter (CVC) system ports that use an open-cell micro-abrasive formaldehyde-melamine-sodium bisulfite foam containing disinfecting solutions.

The present invention was made in view of the prior art described above, and the object of the present invention is to provide a method for simultaneously killing bacteria and removing or reducing the amount of biofilm deposition on medical equipment.

To solve the problem, the present invention provides a method for cleaning medical equipment by scrubbing the equipment with a melamine-formaldehyde foam comprising an antibacterial active composition, wherein the melamine-formaldehyde foam is prepared from a melamine-formaldehyde precondensate, wherein the molar ratio melamine to formaldehyde of the melamine-formaldehyde precondensate is smaller than 0.5.

Preferred embodiments of the method according to the invention are described in claims 2 to 7.

The melamine-formaldehyde foam may be produced by heating and foaming an aqueous mixture M using microwave radiation, said mixture M comprising at least one melamine-formaldehyde precondensate, at least one curative, at least one surfactant, at least one blowing agent. A suitable process is described in WO 2014/037233.

Commercially available melamine-formaldehyde precondensates are useful for a multiplicity of fields of use, for example for further processing into glues. Melamine formaldehyde precondensates comprising sulfite groups are advantageous for use in some of these fields. Such sulfite group-containing melamine-formaldehyde precondensates are obtainable for example as described in EP-B 37470 whereby from 1% to 20% by weight of sodium disulfite is incorporated in the course of the condensation of melamine and formaldehyde to obtain co-condensed sulfite groups.

For the processes of the present invention, however, the melamine-formaldehyde precondensate comprises preferably less than 1 wt.-%, preferably less than 0.1 wt.-% of sulfite groups, most preferably the melamine-formaldehyde precondensate is essentially free of sulfite groups.

The mechanical/elastic properties or the melamine-formaldehyde foams are dependent on the molar melamine to formaldehyde ratio (M:F) of the melamine-formaldehyde precondensate. Preferably the molar ratio melamine to formaldehyde of the melamine-formaldehyde precondensate is smaller than 0.5 and more preferably is in the range from 1:2.1 to 1:3.9 and most preferably in the range from 1:2.5 to 1:3.5. The molar ratio of the melamine to formaldehyde used for preparing the melamine-formaldehyde precondensate may be determined by nuclear magnetic resonance (NMR) spectroscopy and integration of the peak area of the methylene and methylol bridging units.

The melamine-formaldehyde precondensate in addition to melamine and formaldehyde may comprise up to 50% by weight and preferably up to 20% by weight (all based on the weight of co-condensed melamine formaldehyde precondensate) of other thermoset-formers and up to 50% by weight and preferably up to 20% by weight (all based on the weight of co-condensed melamine formaldehyde precondensate) of other aldehydes in co-condensed form. Useful thermoset formers include for example: alkyl- and arylalkyl-substituted melamine, urea, urethanes, carboxamides, dicyandiamide, guanidine, sulfurylamide, sulfonamides, aliphatic amines, glycols, phenol and its derivatives. Examples of useful other aldehydes are acetaldehyde, trimethylolacetaldehyde, acrolein, benzaldehyde, furfurol, glyoxal, glutaraldehyde, phthalaldehyde and terephthalaldehyde. Particular preference is given to an unmodified melamine-formaldehyde precondensate, i.e., a melamine-formaldehyde precondensate devoid of any other thermoset formers or other aldehydes.

Anionic, cationic and nonionic surfactants and also mixtures thereof can be used as emulsifier for the emulsification of the blowing agent and stabilization of the foam.

Useful anionic surfactants include for example diphenylene oxide sulfonates, alkane and alkylbenzenesulfonates, alkylnaphthalenesulfonates, olefinsulfonates, alkyl ether sulfonates, fatty alcohol sulfates, ether sulfates, α-sulfo fatty acid esters, acylaminoalkanesulfonates, acyl isethionates, alkyl ether carboxylates, N-acylsarcosinates, alkyl and alkylether phosphates. Useful nonionic surfactants include alkylphenol polyglycol ethers, fatty alcohol polyglycol ethers, fatty acid polyglycol ethers, fatty acid alkanolamides, ethylene oxide-propylene oxide block copolymers, amine oxides, glycerol fatty acid esters, sorbitan esters and alkylpolyglycosides. Useful cationic emulsifiers include for example alkyltriammonium salts, alkylbenzyldimethylammonium salts and alkylpyridinium salts.

The emulsifiers are preferably added in amounts from 0.2% to 5% by weight, based on the melamine-formaldehyde precondensate.

Preferably a surfactant mixture is used as emulsifier comprising a mixture of 50 to 90 wt.-% of at least one anionic surfactant and 10 to 50 wt.-% of at least one nonionic surfactant, wherein the weight percentages are each based on the total weight of the surfactant mixture. Most preferably a surfactant mixture of 50 to 90 wt. % at least one alkanesulfonate and 10 to 50 wt.-% of at least on alkyl polyethylene glycol ether is used.

As curatives it is possible to use acidic compounds which catalyze the further condensation of the melamine formaldehyde resin. The amount of these curatives is generally in the range from 0.01% to 20% by weight and preferably in the range from 0.05% to 5% by weight, all based on the precondensate. Useful acidic compounds include organic and inorganic acids, for example selected from the group consisting of hydrochloric acid, sulfuric acid, phosphoric acid, nitric acid, formic acid, acetic acid, oxalic acid, toluenesulfonic acids, amidosulfonic acids, acid anhydrides and mixtures thereof.

Preferably formic acid is used as curative.

The mixture comprises a blowing agent. The amount of blowing agent in the mixture generally depends on the desired density for the foam. Preferably the amount in relation to the melamine-formaldehyde precondensate is chosen in an amount that the density of the foam is 8 to 12 kg/m$^3$, more preferably 9 to 11 kg/m$^3$.

In principle, the process of the present invention can use both physical and chemical blowing agents. Useful blowing agents include for example hydrocarbons, such as pentane, hexane, halogenated, more particularly chlorinated and/or fluorinated, hydrocarbons, for example methylene chloride, chloroform, trichloroethane, chlorofluorocarbons, hydrochlorofluorocarbons (HCFCs), alcohols, for example methanol, ethanol, n propanol or isopropanol, ethers, ketones and esters, for example methyl formate, ethyl formate, methyl acetate or ethyl acetate, in liquid form or air, nitrogen or carbon dioxide as gases.

The mixture further comprises at least one blowing agent. This blowing agent is present in the mixture in an amount of 0.5% to 60% by weight, preferably 1% to 40% by weight and more preferably 1.5% to 30% by weight, based on the melamine-formaldehyde precondensate. It is preferable to add a physical blowing agent having a boiling point between 0 and 80° C. Preferably pentane is used as blowing agent.

The precondensate being foamed up generally by heating the suspension of the melamine-formaldehyde precondensate to obtain a foamed material.

The introduction of energy may preferably be effected via electromagnetic radiation, for example via high-frequency radiation at 5 to 400 kW, preferably 5 to 200 kW and more preferably 9 to 120 kW per kilogram of the mixture used in a frequency range from 0.2 to 100 GHz, preferably 0.5 to 10 GHz. Magnetrons are a useful source of dielectric radiation, and one magnetron can be used or two or more magnetrons at the same time.

The mixture to be blown is irradiated immediately on emerging from the foaming die. The blowing agent evaporates, the resin mixture foams up and at the same time cures through. The foamed materials produced are finally dried, removing residual water and blowing agent from the foam. To improve elasticity the foam may be tempered and/or pressed.

The melamine-formaldehyde foam preferably has an open-cell structure. Preferably the melamine-formaldehyde foam has an open-cell content of more than 50% and more particularly more than 95%, when measured according to DIN ISO 4590. Preferably the density of the foam is 8 to 12 kg/m$^3$, more preferably 9 to 11 kg/m$^3$.

The melamine-formaldehyde foam comprises an antibacterial active composition, comprising one or more antibacterial active substances. Suitable antibacterial active substances include alcohols, such as ethanol, hexanol, n-propanol or isopropanol, quaternary ammonium compounds, such as benzalkonium chloride, or halogenated compounds, such as triclosan, 2,4-dichlorbenzyl alcohol, chlorhexidine gluconate or povidone-iodine.

Preferably a solution or dispersion comprising isopropyl alcohol, chlorhexidine gluconate or povidone-iodine or mixtures thereof is used as antibacterial active composition.

Preferably the open-cell melamine-formaldehyde foam comprises from 0.1 to 10 wt.-% of the antibacterial active composition.

The antibacterial active composition or substances may be incorporated to the melamine-formaldehyde foam before the step of foaming a precondensate by heating a solution or dispersion of a melamine-formaldehyde precondensate in the presence of a foaming agent as described in WO 2008/110475 and/or a melamine-formaldehyde foam may be coated or filled with the antibacterial active composition. Preferably the melamine-formaldehyde foam is soaked with a solution or dispersion of the antibacterial active composition and squeezed thereafter.

Preferably the melamine-formaldehyde foam has an open-cell structure which is totally or partially filled with a solution or dispersion comprising isopropyl alcohol, chlorhexidine gluconate or povidone-iodine or mixtures thereof as antibacterial active composition.

The method according to the invention is especially useful for removing biofilm depositions from medical equipment.

Preferably the method is applied for cleaning a catheter or endoscope, most preferably a Central Venous Catheter (CVC) system port, as medical equipment.

EXAMPLES

Hereinafter, the present invention is described in more detail and specifically with reference to the Examples, which however are not intended to limit the present invention.

Test Procedure for Cleaning Test

A test soil based on hand cream and carbon black was prepared and applied to tiles with a doctor blade to yield a film height of 300 µm. The material was subsequently burned onto tiles in an oven at 160° C. for 10 minutes. Tiles prepared by the aforementioned method were cleaned with melamine formaldehyde sponges and the number of strokes needed to remove the soil from the surface was measured.

Ram Pressure Value [N]:

All stamps pressure value measurements for evaluation of the mechanical/elastic properties of the melamine/formaldehyde foams were carried out as follows: one cylindrical steel die with a diameter of 8 mm and a height of 10 cm was applied at right angles in a cylindrical foam sample having a diameter of 11 cm and a height of 5 cm is pressed, to the foam sample broke. Up to the tearing of the foam sample maximum force applied by the plunger (unit: N), in the following also referred to as ram pressure value, provides information about the quality of the foam mechanically/elastic (reported in table 1 in each case the measurements were performed parallel to the rise direction of the foam). The larger the punch pressure values are, the better the mechanical/elastic properties of the melamine/formaldehyde foams.

Materials Used:

Melamine-Formaldehyde Precondensates:

mf-1: The melamine-formaldehyde precondensate mf-1 was a spray-dried melamine-formaldehyde precondensate having an average molecular weight (number average) Mn of 350 g/mol, which had a molar ratio of melamine:formaldehyde of 1:3, which apart from melamine comprised no further thermoset-formers and apart from formaldehyde comprised no further aldehydes and which was sulfite group free.

mf-2: The melamine-formaldehyde precondensate mf-2 was a spray-dried melamine-formaldehyde precondensate having an average molecular weight (number average) Mn of 370 g/mol, which had a molar ratio of melamine:formaldehyde of 1:3, which apart from melamine comprised no further thermoset-formers and apart from formaldehyde comprised no further aldehydes, and which had a sulfite group content of 2.3 wt.-%, based on the total weight of the melamine-formaldehyde precondensate.

mf-3: The melamine-formaldehyde precondensate mf-3 was a spray-dried melamine-formaldehyde precondensate, which had a molar ratio of melamine:formaldehyde of 1:1.6, which apart from melamine comprised no further thermoset-formers and apart from formaldehyde comprised no further aldehydes and which was sulfite group free.

sm-1: Surfactant mixture of 80 wt. % alkanesulfonate mixture and 20 wt.-% alkyl polyethylene glycol ether mixture.

sm-2: Surfactant mixture of 80 wt. % of sodium salt of fatty alcohol polyglycol ether sulfate and 20 wt.-% alkyl polyethylene glycol ether mixture.

Example 1

70 parts by weight of a spray-dried melamine/formaldehyde precondensate mf-1 was dissolved in 30 parts by weight of water. To this mixture was added 2.75 parts by weight of sodium formate, 3.1 parts by weight of formic acid, 1.5 parts by weight of the surfactant mixture sm-1 and 17.8 parts by weight a blowing agent mixture of 80 wt.-% of n-pentane and 20 wt.-% of isopentane. This mixture was stirred vigorously and then foamed in a mould of polypropylene by irradiation of microwave energy at 2.54 GHz. The foam was afterwards cured in an oven at 100° C. and annealed at 240° C.

Example 2

70 parts by weight of a spray-dried melamine/formaldehyde precondensate mf-2 was dissolved in 30 parts by weight of water. To this mixture was added 2.75 parts by weight of sodium formate, 3.1 parts by weight of formic acid, 1.5 parts by weight of the surfactant mixture sm-1 and 17.8 parts by weight a blowing agent mixture of 80 wt.-% of n-pentane and 20 wt.-% of isopentane. This mixture was stirred vigorously and then foamed in a mould of polypropylene by irradiation of microwave energy at 2.54 GHz. The foam was afterwards cured in an oven at 100° C. and annealed at 240° C.

Tiles prepared by the above described test procedure for cleaning test were cleaned with melamine formaldehyde sponges prepared from resins with bisulfite (Example 2) and without bisulfite (Example 1). The sponges were soaked with isopropanol before cleaning, squeezed dry and subsequently the number of strokes needed to remove the soil from the surface was measured. Results are reported in Table 1.

With the foam according to Example 1 only a mean number of 5.7 strokes were needed compared to 8.7 strokes for the foam according to Example 2. Less strokes mean more effective cleaning.

TABLE 1

| melamine-formaldehyde pre-condensate | Example 1 mf-1 (sulfite-group free) | Example 2 mf-2 (sulfite group 2.3 wt.-%) |
| --- | --- | --- |
| Run 1 | 7 | 10 |
| Run 2 | 4 | 7 |
| Run 3 | 6 | 9 |
| Mean number of strokes | 5.7 ± 1.5 | 8.7 ± 1.5 |

Comparative Examples C3 and C4

70 parts by weight of a spray-dried melamine/formaldehyde precondensate mf-3 was dissolved in 30 parts by weight of water. To this mixture was added 2.75 parts by weight of sodium formate, 3.1 parts by weight of formic acid, 1.5 parts by weight of the surfactant mixture sm-2 and 17.8 parts by weight a blowing agent mixture of 80 wt.-% of n-pentane and 20 wt.-% of isopentane. To this blowing agent containing melamine/formaldehyde precondensate 0.1 wt.-% $AgNO_3$, based on the precondensate, was added in case of Example C4. This mixture was stirred vigorously and then foamed in a mould of polypropylene by irradiation of microwave energy at 2.54 GHz. The foam was afterwards cured in an oven at 100° C. and annealed at 240° C.

Comparative Example C5

70 parts by weight of a spray-dried melamine/formaldehyde precondensate mf-3 was dissolved in 30 parts by weight of water. To this mixture was added 2.75 parts by weight of sodium formate, 3.1 parts by weight of formic acid, 1.5 parts by weight of the surfactant mixture sm-1 and 17.8 parts by weight a blowing agent mixture of 80 wt.-% of n-pentane and 20 wt.-% of isopentane. This mixture was stirred vigorously and then foamed in a mould of polypropylene by irradiation of microwave energy at 2.54 GHz. The obtained foam was not stable and collapsed during curing.

Examples 6 and 7

70 parts by weight of a spray-dried melamine/formaldehyde precondensate mf-1 was dissolved in 30 parts by weight of water. To this mixture was added 2.75 parts by weight of sodium formate, 3.1 parts by weight of formic acid, 1.5 parts by weight of the surfactant mixture sm-1 and 17.8 parts by weight a blowing agent mixture of 80 wt.-% of n-pentane and 20 wt.-% of isopentane. To this blowing agent containing melamine/formaldehyde precondensate 0.1 wt.-% $AgNO_3$, based on the precondensate, was added in case of Example 6. This mixture was stirred vigorously and then foamed in a mould of polypropylene by irradiation of microwave energy at 2.54 GHz. The foam was afterwards cured in an oven at 100° C. and annealed at 240° C.

The effect of adding 0.1 wt % $AgNO_3$ as antimicrobial agent was tested by the above described test procedure for cleaning test for M:F ratios of greater (Comparative Examples C3 and C4) and smaller 0.5 (Examples 5 and 6) and summarized in Table 2. In both cases the pristine resins (Examples C3 and 5) perform better than the silver-modified systems (Examples C4 and 6). The mechanical/elastic properties (ram pressure) of systems with M:F <0.5 (Examples 5 and 6) are better and less strokes are needed for cleaning than for systems with M:F >0.5 (Examples C3 and C4).

This finding is also reflected in the mechanical properties according to ram pressure, where typical ram pressures for M:F <0.5 are 30N and 23N without and with 0.1 wt % $AgNO_3$, respectively and for M:F >0.5 are 13N and 7N without and with 0.1 wt % $AgNO_3$, respectively.

TABLE 2

| Example | melamine-formaldehyde precondensate | $AgNO_3$ | Mean number of strokes | Ram pressure [N] |
|---|---|---|---|---|
| C3 | mf-3 (M/F >0.5) | — | 11 | 13 |
| C4 | mf-3 (M/F >0.5) | 0.1 wt.-% | 12 | 7 |
| 6 | mf-1 (M/F <0.5) | — | 5 | 30 |
| 7 | mf-1 (M/F <0.5) | 0.1 wt.-% | 8 | 23 |

The invention claimed is:

1. A method for cleaning medical equipment comprising scrubbing the equipment with a melamine-formaldehyde foam comprising an antibacterial active composition, wherein the melamine-formaldehyde foam is prepared from a melamine-formaldehyde precondensate, wherein the molar ratio melamine to formaldehyde of the melamine-formaldehyde precondensate is smaller than 0.5, wherein the melamine-formaldehyde foam is prepared in the presence of a surfactant mixture comprising 50 to 90 wt. % of at least one alkanesulfonate and 10 to 50 wt.-% of at least one alkyl polyethylene glycol ether, and wherein the medical equipment is a catheter or an endoscope.

2. The method according to claim 1, wherein the melamine-formaldehyde foam has an open-cell structure having an open-cell content, when measured to DIN ISO 4590, of more than 95%.

3. The method according to claim 1, wherein the melamine-formaldehyde foam has a density in the range from 8 to 12 kg/m$^3$.

4. The method according to claim 1, wherein the melamine-formaldehyde foam has an open-cell structure which is totally or partially filled with a solution or dispersion comprising isopropyl alcohol, chlorhexidine gluconate or povidone-iodine or mixtures thereof as antibacterial active composition.

5. The method according to claim 1, wherein the melamine-formaldehyde foam comprises from 0.1 to 10 wt.-% of the antibacterial active composition.

6. The method according to claim 1, wherein the melamine-formaldehyde precondensate is essentially free from sulfite-groups.

7. The method according to claim 1, wherein the molar ratio melamine to formaldehyde of the melamine-formaldehyde precondensate is in the range from 1:2.5 to 1:3.5.

8. The method according to claim 1, wherein a Central Venous Catheter (CVC) system port is used as medical equipment.

* * * * *